(12) United States Patent
Grundei

(10) Patent No.: US 6,482,238 B1
(45) Date of Patent: Nov. 19, 2002

(54) UPPER LEG STUMP ENDOPROSTHESIS FOR AN EXOPROSTHETIC PROVISION

(75) Inventor: Hans Grundei, Lübeck (DE)

(73) Assignee: Eska Implants GmbH & Co. (DE)

( * ) Notice: Subject to any disclaimer, the term of this patent is extended or adjusted under 35 U.S.C. 154(b) by 0 days.

(21) Appl. No.: 09/868,285

(22) PCT Filed: Sep. 10, 1999

(86) PCT No.: PCT/EP99/06676
§ 371 (c)(1),
(2), (4) Date: Jun. 15, 2001

(87) PCT Pub. No.: WO00/35380
PCT Pub. Date: Jun. 22, 2000

(30) Foreign Application Priority Data

Dec. 16, 1998 (DE) .......................... 198 57 907

(51) Int. Cl.⁷ .............................. A61F 2/60; A61F 2/78
(52) U.S. Cl. ......................................... 623/32
(58) Field of Search ............................ 623/32, 28, 27, 623/38, 53

(56) References Cited

U.S. PATENT DOCUMENTS

| | | | | | |
|---|---|---|---|---|---|
| 3,947,897 A | * | 4/1976 | Owens | .................. | 623/32 |
| 4,143,426 A | * | 3/1979 | Hall et al. | .................. | 623/53 |
| 5,041,137 A | * | 8/1991 | Nemoshkalov | .............. | 623/16 |

FOREIGN PATENT DOCUMENTS

| | | | | |
|---|---|---|---|---|
| DE | 31 25 268 | 1/1983 | | |
| DE | 43 38 746 | 5/1995 | | |
| DE | 42 08 247 | 7/1995 | | |
| DE | 19627994 | * 1/1997 | ............... | 623/32 |
| EP | 358056 | * 10/1993 | ............... | 623/27 |
| JP | 01085645 | * 3/1989 | ............... | 623/32 |

* cited by examiner

Primary Examiner—Corrine McDermott
Assistant Examiner—Alvin Stewart
(74) Attorney, Agent, or Firm—Cantor Colburn LLP

(57) ABSTRACT

The invention relates to an upper leg stump endoprosthesis for an exoprosthetic provision of a patient having undergone above-knee amputation. According to the invention, the upper leg stump can be inserted into a shank to which a below-knee prosthesis with a foot part is fitted. The inventive prosthesis includes a proximal shaft which is implantable in a truncated femur; an open-mesh, three-dimensional netting structure covering at least partially the proximal shaft; an adapter connected to a distal end of the proximal shaft; and a substitute condyle element, constituting a replica of a natural condyle of a knee joint, and linked to said shaft by said adapter.

7 Claims, 1 Drawing Sheet

UPPER LEG STUMP ENDOPROSTHESIS FOR AN EXOPROSTHETIC PROVISION

FIELD OF THE INVENTION

This invention relates to a femoral-stump endoprosthesis for the adaptation of exoprosthetic provisions for a patient with an amputated femur.

DESCRIPTION OF THE RELATED ART

It is common practice to fit the femoral stump of the object patient with a funnel or shank consisting for instance of a tough, elastic plastic to which the remainder of the prosthesis such as artificial knee joint, lower leg and foot are attached.

A major problem is the exposure of the femoral stump to pressures bearing on it via the tissue. There is, after all, muscular tissue between the truncated femur and the exterior of the femoral stump which, when moved, is constantly subjected to considerable pressure without such contact contributing to a sensation of natural walking.

The publications DE-A-43 38 746 and DE-C-31 25 268 describe femoral-stump implants aimed at solving the aforementioned problem by inserting in the femoral stump a shaft section which is permanently fastened in the bone canal. At its distal end the implant is provided with an enlarged, mushroom-shaped head which is thought to distribute the load over a larger area. Compared to traditional adaptation options this type of adaptation would hold the promise of improved wearing comfort, even though the sensation felt by the patient concerned has practically nothing in common with the natural sensory perception before the amputation.

SUMMARY OF THE INVENTION

Against that background it is the objective of this invention to improve on the femoral-stump endoprosthesis first above mentioned in a way as to significantly enhance the sensory perception of the patient to where walking feels more natural.

The present invention provides a femoral-stump endoprosthesis for an exoprosthetic provision for a patient with an amputated femur. The endoprosthesis can be inserted in a shank to which connects the replicated kneejoint, lower-leg and foot prosthesis. The endoprosthesis includes a proximal shaft which is implantable in a truncated femur; an open-mesh, three-dimensional netting structure covering at least partially said proximal shaft; an adapter connected to a distal end of said proximal shaft; and a substitute condyle element, constituting a replica of a natural condyle of a knee joint, and linked to said shaft by said adapter.

Specifically, the endoprosthesis incorporates a proximal shaft which is implantable in a femoral stump, which is at least partially covered with textured three-dimensional netting and which is provided at its distal end with a cone-shaped adapter serving to link a metallic substitute condyle, replicating the natural condyles of a knee joint, with the said shaft.

The three-dimensional open-mesh netting, also referred to as interconnective netting, permits natural bone tissue to grow into, through, behind and around it during the adaptive healing process whereby, after a relatively brief period—at least with regard to the substrate flow—the implanted shaft section will be integrated in the femur, ensuring extremely sturdy secondary fixation. Growing bone tissue into an open-mesh, three-dimensional netting is a process essentially known in the field of pure endoprosthetics. In that context, reference is made for instance to the German patent DE-PS 41 06 971.

The cone-shaped adapter provided at the distal end permits the attachment of a solid element, i.e. the substitute condyle. The adapter cone is composed of a conical collet with a conical clamping tenon, where the collet may be made a part of the shaft section while the tenon is integrated into the substitute condyle.

The substitute condyle distributes the pressure load over a larger area, while especially the replication of the natural condyles results in a more natural feeling, known as osteoperception, on the part of the patient.

The effect is further enhanced by the fact that the lining of the shank which is fitted over the femoral stump simulates the shape of the natural femoral sliding parts within a natural knee joint. Replicating in the substitute condyle the shape of natural condyles provides the clamping for the simulated sliding parts, substantially improving the bonding of the femoral stump of the patient while walking.

In an advantageous form of implementation, the substitute condyle consists of a basic metal body coated with an impact-absorbing plastic layer. This impact-absorbing layer prevents shocks from reaching the remaining femoral stump unattenuated. It can also help improve osteoperception, considering that in the case of a healthy person as well, shocks to which the knee and ankle joints are exposed are not transmitted to the femur unattenuated.

To be effective, the impact-absorbing layer is preferably 3 to 10 mm thick.

In a particularly preferred embodiment, the impact-absorbing layer consists of silicone, a material which has inherently resilient buffering properties and is extremely well suited to the application within the scope of this invention.

BRIEF DESCRIPTION OF THE DRAWINGS

Referring now to the drawings wherein like elements are numbered alike in the several FIGURES.

Figure 1:
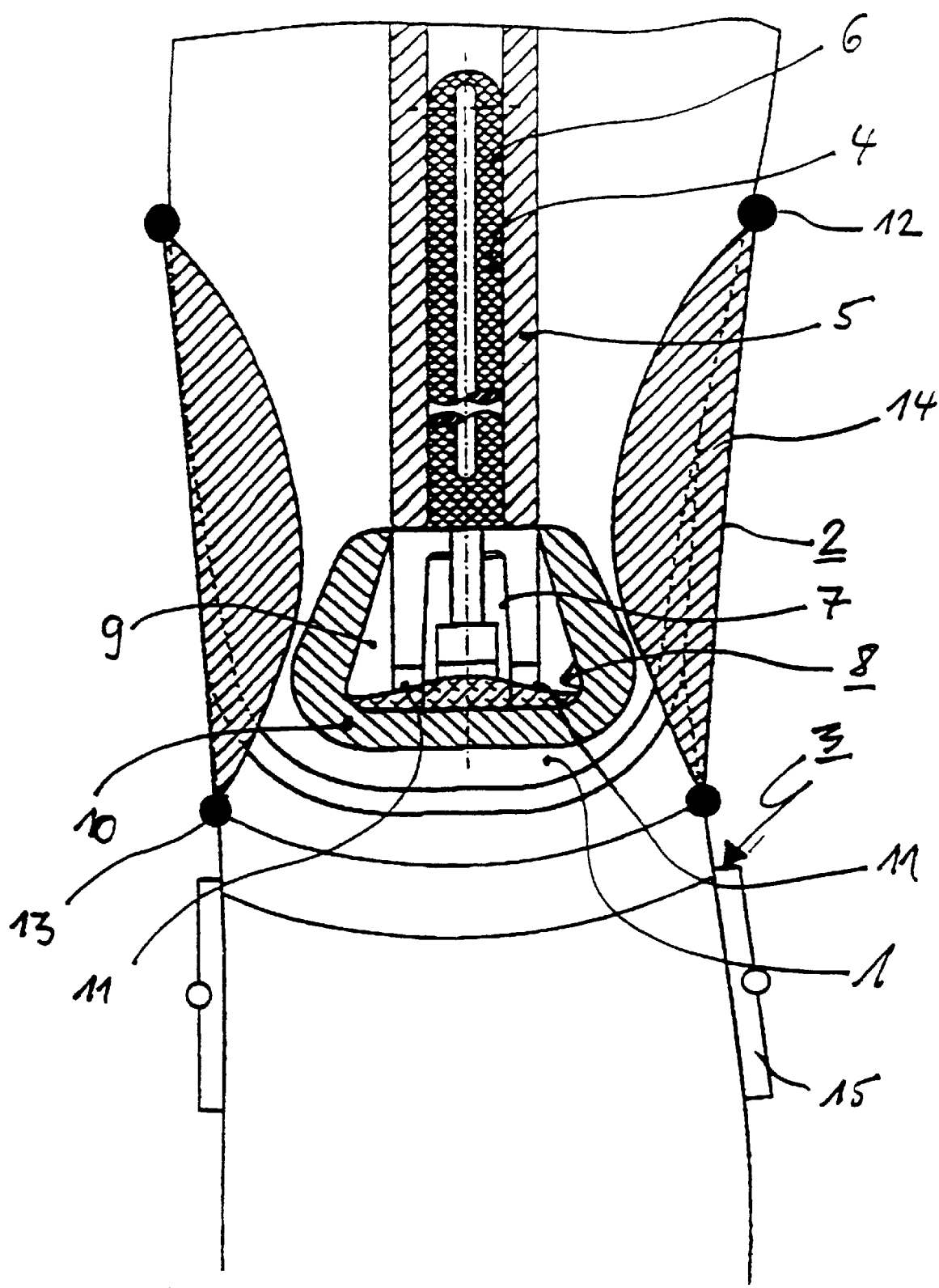
FIG. 1 is schematic view of a femoral stump with a femoral stump endoprosthesis implanted in a truncated femur.

The following will explain this invention in more detail with the aid of one drawing.

The drawing is a schematic illustration of a femoral stump 1, with a femoral-stump endoprosthesis implanted in the truncated femur 5.

DETAILED DESCRIPTION OF THE PREFERRED EMBODIMENT

FIG. 1 is a schematic illustration of a femoral stump 1, with a femoral-stump endoprosthesis implanted in the truncated femur 5.

The proximal section of an intramedullar shaft 4 is implanted in the truncated femur 5. The surface of the shaft section 4 is covered with an open-mesh, three-dimensional netting 6 through which bone tissue can grow so that after a certain adaptive healing period, with respect to the substrate flow, the implanted section of the shaft 4 will have become a more or less integral part of the natural bone.

At its distal end, the shaft 4 connects to a cone-shaped adapter 7. By way of this cone-shaped adapter 7 the distal end of the shaft 4 is linked to the substitute condyle 11 (sic).

The substitute condyle element 8 is configured in such fashion that it replicates the shape of natural condyles 11 in a knee joint.

In the design example illustrated, the substitute condyle element 8 is coated with an impact-attenuating silicone layer 10.

The entire femoral-stump endoprosthesis is thus positioned within the femur. There is no gap anywhere in the area of the femoral stump.

The femoral stump 1 is encased in a femoral shank 2 to which the assembly 3 of artificial knee, lower leg and foot is attached.

The counterpart to the condyle element 8 with its replica of a natural condyle 11 is a correspondingly matched section in the interior of the shank 2 which simulates the natural sliding parts of a knee joint.

The femoral shank 2 in this case consists of pressure padding 14 laterally and medially fitted on the femoral stump and firmly locked onto the femoral stump by means of a clasp 12 and a tiltable hinge 13.

The knee-joint function per se is provided by an artificial knee joint 15 for instance as described in EP-C-0 358 056.

What is claimed is:

1. Femoral-stump endoprosthesis for adaptation of an exoprosthetic provision for a patient with an amputated femur, whereby a femoral stump is enclosable in a shank to which connects a replicated kneejoint, lower-leg and foot prosthesis, said endoprosthesis comprising:
    a proximal shaft which is implantable in a truncated femur;
    an open-mesh, three-dimensional netting structure covering at least partially said proximal shaft;
    an adapter connected to a distal end of said proximal shaft; and
    a substitute condyle element, comprising a replica of a natural condyle of a knee joint, and linked to said shaft by said adapter.

2. Femoral-stump endoprosthesis as in claim 1, wherein said substitute condyle element comprises a basic metal body.

3. Femoral-stump endoprosthesis as in claim 2, wherein said basic metal body is coated with an impact-attenuating plastic layer.

4. Femoral-stump endoprosthesis as in claim 3, wherein said impact-attenuating layer is 3 to 10 mm thick.

5. Femoral-stump endoprosthesis as in claim 4 wherein said impact attenuating layer comprises silicon.

6. Femoral-stump endoprosthesis as in claim 3, wherein said impact attenuating layer comprises silicon.

7. Femoral-stump endoprosthesis as in claim 1, wherein said adapter is of a cone shape.

* * * * *